United States Patent
Garner et al.

(10) Patent No.: US 6,433,007 B1
(45) Date of Patent: Aug. 13, 2002

(54) METHODS FOR THE PREVENTION AND TREATMENT OF POST-SURGICAL COMPLICATIONS

(75) Inventors: Wiliam H. Garner, Southlake; Gustav Graff, Cleburne, both of TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/830,833

(22) PCT Filed: Dec. 10, 1999

(86) PCT No.: PCT/US99/29443

§ 371 (c)(1),
(2), (4) Date: May 1, 2001

(87) PCT Pub. No.: WO00/35433

PCT Pub. Date: Jun. 22, 2000

Related U.S. Application Data

(60) Provisional application No. 60/112,666, filed on Dec. 17, 1998.

(51) Int. Cl.[7] .............................................. A61K 31/35
(52) U.S. Cl. ........................ 514/454; 514/458; 514/912
(58) Field of Search ................................ 514/454, 458, 514/912

(56) References Cited

U.S. PATENT DOCUMENTS

| | | | |
|---|---|---|---|
| 4,550,022 A | 10/1985 | Garabedian et al. | 424/127 |
| 5,607,966 A | 3/1997 | Hellberg et al. | 514/458 |
| 5,643,943 A | 7/1997 | Gamache et al. | 514/456 |
| 5,798,356 A | 8/1998 | Doshi | 514/249 |
| 5,811,438 A | 9/1998 | Hellberg et al. | 514/458 |
| 5,811,453 A | 9/1998 | Yanni et al. | 514/458 |

FOREIGN PATENT DOCUMENTS

| | | |
|---|---|---|
| WO | WO 96/20187 | 7/1996 |
| WO | WO 97/10236 | 3/1997 |
| WO | WO 98/26777 | 6/1998 |

OTHER PUBLICATIONS

Beebe, et al., Control of lens cell differentiation and ion fluxes by growth factors. *Prog. Clin. Biol. Res.*, vol. 217A, pp. 365–369 (1986).

Chamberlain, et al., Evidence that fibroblast growth factor promotes lens fibre differentiation. *Curr. Eye Res.*, vol. 6, pp. 1165–1169 (1987).

Cherfan et al., Nuclear sclerotic cataract after vitrectomy for idiopathic epiretinal membranes causing macular pucker, *Am. J. Ophthalmol.*, vol. 111, pp. 434–438 (1991).

CRC Handbook of Eicosanoids: Prostaglandins, and Related Lipids, vol. II, Drugs Acting Via the Eicosanoids, pp. 59–133, CRC Press, Boca Raton, FL (1989).

Dana et al., "Posterior Capsule Opacification after Cataract Surgery in Patients with Uveitis", *Ophthalmology*, 104(9), pp 1387–1397 (1997).

Dobbs, R.E., et al., Evaluation Of Lens Changes In Idiopathic Epiretinal Membrane, vol. 5, Nos. 1 & 2, pp. 143–148 (1988).

Foulds WS. Is your vitreous really necessary? The role of vitreous in the eye with particular reference to retinal attachment, detachment, and the mode of action of vitreous substitutes. *Eye*, vol. 1, pp. 641–664 (1987).

Hales, et al., Cataract induction in lenses cultured with transforming growth factor–beta. *Invest. Ophthalmol. Vis. Sci.*, vol. 36, pp. 1709–1713 (1995).

Hellberg et al., "Novel Esters and Amides of Nonsteroidal Anriinflammatory Carboxylic Acids as Antioxidants and Antiproliferative Agents", *J. Med. Chem*, 42(2), pp 267–276 (1999).

Ionides et al., "Posterior Capsule Opacification Following Diabetic Extracapsular Cataract Extraction", *Eye*, 8(PT 5), pp 535–537 (1994).

Koch et al., Development of Lens Opacities in a Period of 6 Months After Pneumatic Retinopexy, *Fortschr. Ophthalmol.*, vol. 88, No. 3, pp. 216–218 (1991).

Kreiger, A.E., Wound Complications In Pars Plana Vitrectomy, *Retina*, vol. 13, No. 4, pp. 335–344 (1993).

Kuszak et al., Lens optical quality is a direct function of lens sutural architecture. *Invest. Ophthalmol. Vis. Sci.*, vol. 32, pp. 2119–2129 (1991).

Lipner, Phakic dwellngs: Rdecorating the ocular interior with vision–bosting designs, www.eyeworld.org, vol. 3, No. 11, pp 40–43 (1998).

Peek, et al., Rise and fall of crystallin gene messenger levels during fibroblast growth factor induced terminal differentiation of lens cells. *Dev. Biol.*, vol. 52, pp. 152–160 (1992).

Phelps–Brown NA, et al., Aetiological classification of cataract: ocular, toxic, nutritional and physical factors, and senile cataract In: Phelps–Brown NA, bron AJ, eds. Lens Disorders: *A Clinical Manual of Cataract Diagnosis*. Oxford: Butterworth–Herine,amm Ltd. pp. 190–211 (1996).

Ruellan et al., Cataract and Implantation in the Vitrectomized Eyes, *J. Fr. Ophtalmol.*, vol. 16, issue 5, pp. 315–319 (1993).

Thompson, J.T., et al., Progression of Nuclear Sclerosis and Long–term Visual Results of Vitrectomy With Transforming Growth Factor Beta–2 for Macular Holes, *Am. J. Ophthalmol.*, vol. 119, pp. 48–54 (1995).

Weiner, A.L., Polymeric Drug Delivery Systems For the Eye, in *Polymeric Site–specific Pharmacotherapy*, Ed., A.J. Domb, John Wiley & Sons, pp. 316–327 (1994).

Wickström, et al., The effect of transforming growth factor–alpha (TGF alpha) on rabbit and primate lens epithelial cells in vitro. *Curr. Eye Res.*, vol. 12, pp. 1123–1129 (1993).

*Primary Examiner*—Zohreh Fay
(74) *Attorney, Agent, or Firm*—Gregg C. Brown

(57) ABSTRACT

Methods for treating post-surgical formation of cataracts or posterior capsule opacification are disclosed. The methods utilize compositions containing certain compounds having an anti-inflammatory and anti-oxidant moiety covalently linked by and amide and ester bond.

16 Claims, No Drawings

METHODS FOR THE PREVENTION AND TREATMENT OF POST-SURGICAL COMPLICATIONS

CROSS REFERENCE TO RELATED APPLICATIONS

Applicants claim priority based on International Application Number PCT/US99/29443 filed on Dec. 10, 1999, and U.S. Provisional Patent Application Ser. No. 60/112,666 filed on Dec. 17, 1998.

BACKGROUND OF THE INVENTION

The present invention is directed to methods for the prevention, reduction or amelioration of surgery-induced formation of cataract or posterior capsular opacification.

Various ocular surgeries are performed in an effort to improve vision. Some ocular surgeries. however, such as vitrectomy (posterior-segment surgery), cataract surgery or refractive surgery. may result in the development of post-surgical complications involving the formation of posterior subcapsular cataract ("PSC") and posterior capsule opacification Refractive surgery typically involves the modification of the cornea in myopic patients to correct the focus of light on the retina. Examples of such surgeries include radial keratotomy (radial slices in the cornea), photorefractive keratotomy (laser ablation of the epitheilial and stromal layers of the cornea), LASIK (slicing a cornea flap and removing part of the stromal layer followed by the replacement of the flap), as well as procedures involving the insertion of corneal rings or phakic intraocular lens ("IOL"). During these and other corneal surgeries the cornea is typically bathed with a surgical irrigating solution. Due to the traumatic insult of such procedures, however. various inflammatory events or other tissue or cellular complications may arise. See. e.g., Lipner. Phakic dwellings: Redecorating the ocular interior with vision-bosting designs, www.eyeworld.org, volume 3, number 11, pages 40–43 (1998).

Cataract surgery involves the removal of the cataractous lens and replacement with an IOL. In such surgeries the entire lens is removed in one piece, or the lens is broken down into smaller pieces and suctioned out of the lens capsule by phacoemulsification techniques. In some cases following surgery, however, opacification of the posterior capsule forms, inhibiting clear vision and potentially necessitating further surgery.

Vitrectomylposterior segment surgery procedures are performed for a variety of reasons to correct visual acuity deprivation arising from age-related degenerative processes and other disease processes including diabetes, proliferative vitreoretinopathy (PVR), and trauma-induced retinal hemorrhage.

Vitrectomy involves the removal of the vitreous of the eye, and replacement with another fluid. Vitrectomies are typically performed with the SERIES TEN THOUSAND® OCUTOME® or ACCURUS® posterior-segment surgical systems (Alcon Laboratories, Inc.), or similar instrument, wherein an aspirating, cutting and irrigation probe is inserted through the side of the globe. The instrument cuts and aspirates the vitreous while concurrently replacing the vitreous fluid with a surgical irrigation solution (e.g., BSS PLUS® Surgical Irrigation Solution). Following vitrectomy, the fluid of the posterior segment may be replaced by silicone oil (Foulds WS. Is your vitreous really necessary? The role of vitreous in the eye with particular reference to retinal attachment, detachment, and the mode of action of vitreous substitutes. *Eye*, volume 1, pages 641–664 (1987) or gas tamponade (Phelps-Brown N A, et al., Aetiological classification of cataract: ocular, toxic, nutritional and physical factors, and senile cataract In: Phelps-Brown N A, Bron A J, eds. Lens Disorders: *A Clinical Manual of Cataract Diagnosis*. Oxford: Butterworth-Herine,amm Ltd. pages 190–211, 1996; Ruellan et al., Cataract and Implantation in the Vitrectomized Eyes, *J. Fr. Ophtalmol.*, volume 16, issue 5, pages 315–319 (1993); and Koch et al., Development of Lens Opacities in a Period of 6 Months After Pneumatic Relinopexy, *Fortschr. Ophthalmol.*, volume 88, No. 3, pages 216–218 (1991)) in order to achieve/maintain retinal attachment.

Vitrectomy can induce a variety of post-surgical complications. Many of these complications are further potentiated in diabetic patients who are at risk for many ocular pathologies. Due to the severity of the surgical procedure, the posterior segment surgery process can cause tissue damage at both the acute and chronic phases of the recovery. Tissue edema generally occurs during the post-surgical acute phase. This is caused by breakdown of the blood aqueous and blood retinal barrier functions resulting in sustained vascular permeability and accumulation of plasma constituents in the ocular compartments following the surgical trauma. Slit-lamp clinical examinations at 24 hours have indicated extensive anterior chamber flare and cell influx, conjunctival congestion and swelling (with discharge), iritis, corneal haze and cataract formation. See for example, Kreiger, A. E., Wound Complications In Pars Plana Vitrectomy *Retina*, volume 13, No. 4, pages 335–344 (1993); Cherfan et al., Nuclear sclerotic cataract after vitrectomy for idiopathic epiretinal membranes causing macular pucker, *Am. J. Ophthalmol.*, volume 111, pages 434–438 (1991); Thompson, J. T., et al., Progression of Nuclear Sclerosis and Long-term Visual Results of Vitrectomy With Transforming Growth Factor Beta-2 for Macular Holes, *Am. J. Ophthalmol.*, volume 119, pages 48–54 (1995) and Dobbs, R. E., et al., Evaluation Of Lens Changes In Idiopathic Epiretinal Membrane, volume 5, Nos. 1 & 2, pages 143–148 (1988).

A disruption of the blood-ocular barriers and influx/or local release of growth factors occurs during inflammatory ocular pathology/or surgical trauma. Such fluid disruption and inflow of growth factors is suspected to play a key role in the development of cataract. (See generally, Beebe, et al., Control of lens cell differentiation and ion fluxes by growth factors. *Prog. Clin. Biol. Res.*, volume 217A, pages 365–9 (1986); Chamberlain, et al., Evidence that fibroblast growth factor promotes lens fibre differentiation. *Curr. Eye Res.*, volume 6, pages 1165–9 (1987); Hales, et al., Cataract induction in lenses cultured with transforming growth factor-beta. *Invest. Ophthalmol. Vis. Sci.*, volume 36, pages 1709–13 (1995); Peek, et al., Rise and fall of crystallin gene messenger levels during fibroblast growth factor induced terminal differentiation of lens cells. *Dev. Biol.*, volume 52, pages 152–60 (1992); and Wickström, et al., The effect of transforming growth factor-alpha (TGF alpha) on rabbit and primate lens epithelial cells in vitro. *Curr. Eye Res.*, volume 12, pages 1123–9 (1993).)

In fact, there is a high incidence (approximately 80%) of post-vitrectomy cataract formation and loss of visual acuity in patients reviewed over a period of 6 to 99 months post-vitrectomy (Cherfan, et al., *Am. J. Ophthalmol.*, volume 111, pages 434–438 (1991)). It is now recognized that this PSC is the consequence of abnormal, post-surgical lens fiber growth resulting in a distortion and branching of line sutures (Kuszak et al., Lens optical quality is a direct function of lens sutural architecture. *Invest. Ophtalmol. Vis. Sci.*, volume 32, pages 2119–2129 (1991). Continued abnormal lens fiber cell growth leads to a progressive decay of lens optical properties due to localized suture defects in newly formed lens fiber layers.

U.S. Pat. No. 5,607,966 (Hellberg et al.), U.S. Pat. No. 5,643,943 (Gamache et al.), U.S. Pat. No. 20 5,811,438 (Hellberg et al.) and U.S. Pat. No. 5,811,453 (Yanni et al.) disclose bifunctional compounds, compositions and methods of use for the treatment of ocular inflammation. The compounds disclosed in these patents are useful in the methods of the present invention. However, these patents do not disclose specific methods of preventing surgery-induced formation of PCO or PSC, using systemic, topical or surgical irrigating solutions of the present invention. The inventors of the present invention have surprisingly found that methods involving the administration of compositions containing compounds disclosed in the preceding patents prevent or reduce the incidence of post-surgical cataract formation.

SUMMARY OF INVENTION

The present invention provides methods of preventing or ameliorating post-surgical formation of PCO or PSC. The methods involve the administration of compositions comprising bifunctional compounds. The compositions may be administered prior to, during, or following surgery, or any combination thereof.

The bifunctional compounds of the present invention include both a non-steroidal anti-inflammatory agent ("NSAIA") moiety and an anti-oxidant moiety. The compositions used in the present invention are topical ophthalmic and surgical irrigating solutions.

DETAILED DESCRIPTION OF INVENTION

The bifunctional compounds useful in the methods of the present invention are of the formula (I):

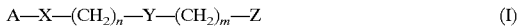

A—X—$(CH_2)_n$—Y—$(CH_2)_m$—Z      (I)

wherein:

A is an non-steroidal anti-inflammatory agent (NSAIA) originally having a carboxylic acid;

A—X is an ester or amide linkage derived from the carboxylic acid moiety of the NSAIA, wherein X is O or NR;

R is H, $C_1$–$C_6$ alkyl or $C_3$–$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is:

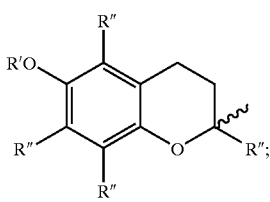

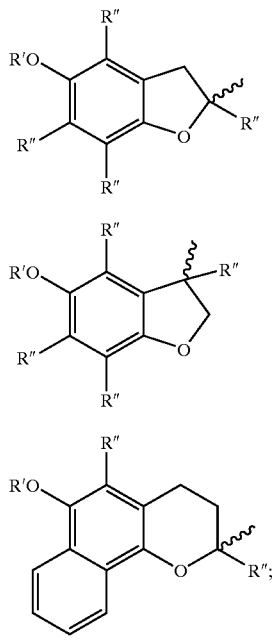

wherein:

R' is H, C(O)R, $C(O)N(R)_2$, $PO_3^-$, or $SO_3^-$; and

R" is H or $C_1$–$C_6$ alkyl.

The bifunctional compounds of the present invention also include various stereoisomers or racemic mixtures of any of the compounds contemplated within formula (I), and pharmaceutically acceptable salts of the compounds of formula (I).

The bifunctional compounds of the present invention contain a non-steroidal anti-inflammatory agent, "A", originally having a carboxylic acid moiety. A number of chemical classes of non-steroidal anti-inflammatory agents have been identified. The following text, the entire contents of which are incorporated herein by reference to the extent it refers to NSAIAs having a carboxylic acid, may be referred to for various NSAIA chemical classes: *CRC Handbook of Eicosanoids: Prostaglandins, and Related Lipids, Volume II. Drugs Acting Via the Eicosanoids*, pages 59–133, CRC Press, Boca Raton, Fla. (1989). The NSAIA may be selected, therefore, from a variety of chemical classes including, but not limited to, fenamic acids, such as flufenamic acid, niflumic acid and mefenamic acid; indoles, such as indomethacin, sulindac and tolmetin; phenylalkanoic acids, such as suprofen, ketorolac, flurbiprofen, ibuprofen and diclofenac. Further examples of NSAIAs are listed below:

| loxoprofen | tolfenamic acid | indoprofen |
| pirprofen | Clidanac | fenoprofen |
| naproxen | Fenclorac | meclofenamate |
| benoxaprofen | Carprofen | isofezolac |
| aceloferac | Fenbufen | etodolic acid |
| fleclozic acid | Amfenac | efenamic acid |
| bromfenac | Ketoprofen | fenclofenac |
| alcofenac | Orpanoxin | zomopirac |
| diflunisal | pranoprofen | zaltoprofen |

The preferred compounds of formula (I) are those wherein "A" is selected from the ester or amide derivatives of naproxen, flurbiprofen or diclofenac. The most preferred compounds are those wherein "A" is selected from the ester or amide derivatives of naproxen or flurbiprofen.

With respect to the other substituents of the compounds of formula (I), the preferred compounds are those wherein:

X is O or NR;

R is H or $C_1$ alkyl;

Y is CH(OH), and m is 0 to 2 and n is 1 or 2, or Y is not present, and m is 1 or 2 and n is 0 to 4;

Z is a, b or d;

R' is H or $C(O)CH_3$; and

R" is $CH_3$.

The most preferred compounds are those wherein:

X is O or NR;

R is H;

Y is not present;

m is 0 or 1;

n is 1;

Z is a, or b;

R' is H; $C(O)CH_3$; and

R" is $CH_3$.

The following compounds are particularly preferred:

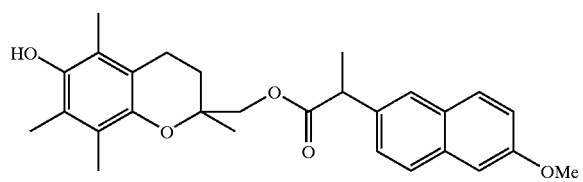

2-(6-hydroxy-2,5,7,8-tetramethyl-3,4-dihydro-2H-benzo[1,2-b]pyran-2-yl)methyl 2-(6-methoxy-2-naphthyl)propionate ("Compound A");

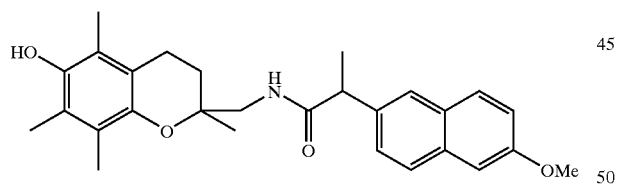

N-(2-(6-hydroxy-2,5,7,8-tetramethyl-3,4-dihydro-2H-benzo[1,2-b]pyran-2-yl)methyl) 2-(6-methoxy-2-naphthyl)propionamide ("Compound B");

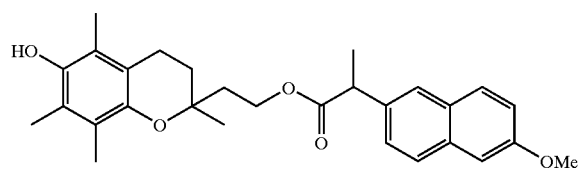

2-(6-hydroxy-2,5,7,8-tetramethyl-3,4-dihydro-2H-benzo[1,2-b]pyran-2-yl)ethyl 2-(6-methoxy-2-naphthyl)propionate ("Compound C");

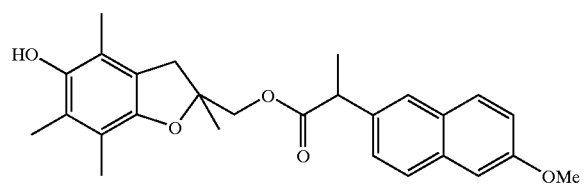

2-(5-hydroxy-2,4,6,7-tetramethyl-2,3-dihydro-benzo[1,2-b]furan-2-yl)methyl 2-(6-methoxy-2-naphthyl)propionate ("Compound D");

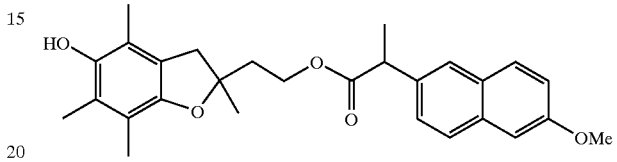

2-(5-hydroxy-2,4,6,7-tetramethyl-2,3-dihydro-benzo[1,2-b]furan-2-yl)ethyl 2-(6-methoxy-2-naphthyl)propionate ("Compound E");

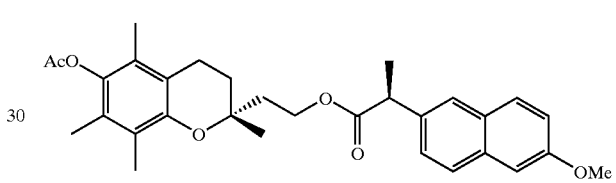

2-(6-hydroxy-2,5,7,8-tetramethyl-2,3-dihydro-2H-benzo[1,2-b]pyran-2-yl)ethyl 2-(3-fluoro-4-phenyl-phenyl)propionate ("Compound F");

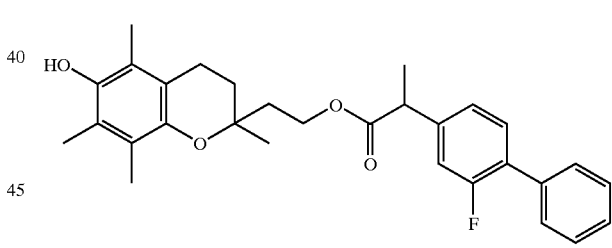

(S)-6-methoxy-□-methyl-naphthaleneacetic acid, (R)-2-(6-acetoxy-3,4-dihydro-2,5,7,8-tetramethyl-2H-1-benzopyran-2-yl)ethyl ester ("Compound G"); and (R)N-(2-(6-acetoxy-2,5,7,8-tetramethyl-3,4-dihydro-2H-benzo[1,2-b]pyran-2-yl)methyl) (S) (2-(6-methoxy-2-naphthyl)propionamide ("Compound H").

The most preferred bifunctional compound of the present invention is:

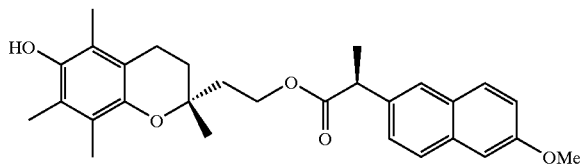

(S)-6-methoxy-☐-methyl-naphthaleneacetic acid, (R)-2-(3,4-dihydro-6-hydroxy-2,5,7,8-tetramethyl-2H-1-benzopyran-2-yl)ethyl ester ("Compound X"), which is a particular stereoisomer of Compound C.

The compounds of formula (I) possess antinflammatory, antioxidant and antiproliferative activity. The compounds of formula (I) may be prepared by methods disclosed in U.S. Pat. No. 5,607,966 (Hellberg et al.), the entire contents of which are incorporated herein by reference.

As stated above, the present invention is directed to methods employing compositions adapted for the prevention or amelioration of PCO or PSC. The compositions of the present invention will be applied to the eye of a mammal prior to, during or following ocular surgery, or combinations thereof. When the compositions are administered prior to, or following surgery, they generally will be topically applied to the eye. When the compositions are applied during surgery, they will generally be applied intraocularly via a surgical irrigating solution and, optionally, topically as well. The compounds of formula (I), however, may also be dosed systemically. Such administration will generally involve oral or intravenous routes. Oral doses will generally be administered prior to and/or following surgery, and intravenous doses will generally be administered prior to, during and/or following surgery.

The compositions of the present invention will include one or more compounds of formula (I) and a pharmaceutically acceptable vehicle for said compound(s).

Topical ophthalmic compositions will be employed when the compounds are to be dosed topically. The preparation of topical ophthalmic compositions is well known in the art. Generally, topical ophthalmic compositions useful in the present invention will be in the form of a solution, suspension, gel, or formulated as part of a device, such as a collagen shield or other bioerodible or non-bioerodible device. Various excipients may be contained in the topical ophthalmic solutions, suspensions or gels of the present invention. For example, buffers (e.g., borate, carbonate, phosphate), tonicity agents (e.g., sodium chloride, potassium chloride, polyols), preservatives (e.g., polyquaterniums, polybiguanides, BAC), chelating agents (e.g., EDTA), viscosity enhancing agents (e.g., polyethoxylated glycols) and solubilizing agents (e.g., polyethoxylated castor oils, including polyoxl-35 castor oil (Cremophor EL®, BASF Corp., Parsippany, N.J.); Polysorbate 20, 60 and 80; Pluronic® F-68, F-84 and P-103 (BASF Corp.); or cyclodextrin) may be included in the topical ophthalmic compositions. A variety of gels may be useful in topical ophthalmic gel compositions of the present invention, including, but not limited to, carbomers, polyvinyl alcohol-borates complexes, or xanthan, gellan, or guar gums. Topical ophthalmic bioerodible and non-bioerodible devices (e.g., conjunctival implant) are known in the art and may be useful in the topical administration of formula (I) compounds. See, for example, Weiner, A. L., Polymeric Drug Delivery Systems For the Eye, in *Polymeric Site-specific Pharmacotherapy*, Ed., A. J. Domb, John Wiley & Sons, pages 316–327 (1994). While the particular ingredients and amounts to be contained in topical ophthalmic compositions useful in the methods of the present invention will vary, particular topical ophthalmic compositions will be formulated to effect the administration of a compound of formula (I) topically to the eye.

The use of irrigating solutions as pharmaceutical vehicles for the compounds of formulas (I) is preferred when the compositions are administered intraocularly. The most basic irrigating solutions generally comprise saline, or phosphate-buffered saline. More advanced irrigating solutions, however, are preferred. As used herein, the term "physiologically balanced irrigating solution" refers to a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a bicarbonate-buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.) the entire contents of which are incorporated herein by reference.

Oral formulations of the compounds of formula (I) will generally comprise compressed solid or gelatin tablets. Methods for the preparation of such oral tablet vehicles are well known by those skilled in the art. Intravenous compositions useful in the present invention will generally be aqueous formulations which provide for the solubilization and stabilization of a compound of formula (I). Methods for the preparation of such intravenous vehicles are well known by those skilled in the art.

Any of the above-described vehicles or other ophthalmic vehicles known in the art may be employed in the compositions of the present invention, provided such vehicles allow for the administration of a compound of formula (I) to the eye and do not cause significant side effects to the patient. As used herein, such a vehicle is referred to as a "pharmaceutically acceptable vehicle."

The concentrations of the formula (I) compounds in the compositions will depend on various factors, including type of composition, and the nature and severity of the condition requiring surgery. The formula (I) compounds and compositions of the present invention, however, will be employed in a therapeutically effective amount. As used herein, a "therapeutically effective amount" is that amount required to prevent, reduce or ameliorate post-surgical cataract formation. Irrigation solutions will generally contain one or more of the compounds of formula (I) in a concentration of from about 0.01 μM to about 100 μM. Preferred irrigation solutions will have a formula (I) concentration of about 0.1 to 5.0 μM. Topical ophthalmic compositions will generally have a formula (I) compound concentration of from about 0.01%–1.0% w/v.

As stated above, the methods of the present invention involve the administration of a compound of formula (I) to the eye to prevent or treat post-surgical PCO or PSC formation. Such methods may involve the pre-surgical application of a topical ophthalmic formulation to the eye. Such regimens may involve dosing the eye with 1–2 drops, 1–4 times a day for up to a week prior to surgery. Administration of the compounds of formula (I) during surgery may involve the application of irrigating solutions intraocularly and, optionally, the periodic, concurrent administration of a topical ophthalmic composition to the cornea or conjunctiva (or use of a conjunctival implant containing a composition of the present invention). Administration of the compounds of formula (I) post-surgery, may involve topical dosing of 1–2 drops, 1–4 times a day, for about 1–4 weeks following surgery.

Optionally, the compositions of the present invention may be administered systemically prior to, during or following surgery, or combinations thereof and, either alone, or concurrently with the topical or intraocular regimens described above. Systemic methods may involve orally dosing the mammal 1–4 times a day with dosages of about 0.1–300 mg/kg, for up to 1 week prior to surgery and 1 week following or, in the case of intravenous administration, dosing the mammal with about 0.1–300 mg/kg, during or following surgery.

EXAMPLE 1

The following example illustrates the reduction in frequency of post-vitrectomy cataract formation, employing a surgical irrigating solution containing a compound of formula (I).

Age-matched, Dutch Belted rabbits were used in this study. At 2.5 months of age, unilateral, partial vitrectomy (vitreous replaced by irrigating solution) was performed. Briefly, rabbits (1.5–2.0 kg) were prepared for surgery by subcutaneous administration of atropine to maintain heart rate and limit lung and oropharynx fluid accumulation. Animals were then anesthetized by intramuscular administration of ketamine (45 mg/kg) and xylazine (6 mg/kg). Anesthesia was maintained by re-administration of half-doses of anesthetic every 35–45 minutes as needed. For pupil dilatation, phenylephrine HCL and cyclopentolate HCL were administered topically to the surgical eye (OD). The nonsurgical eye (OS) received Duratears and was then taped shut to prevent loss of moisture. Immediately prior to surgery, proparacaine was administered topically to the OD eye and a speculum inserted. Conjunctival tissue was incised 2 mm from the limbus near the superior rectus muscle (3 to 9 o'clock position) and reflected. Two sutures were placed in a figure eight (4 and 8 o'clock position), about 4.5 mm from the limbus, to accommodate the outer port suction cutter and endoilluminator, respectively. An inner port infusion cannula was sutured through the pars plana (6 o'clock position) about 4 mm from the limbus. Two additional punctures were made with a V-lance stiletto knife (20 gauge) for the instrument entry through the outer ports. Two sutures were then placed (3 and 9 o'clock position) in the sclera, approximately 1 mm from the limbus, to facilitate manipulation of the eye and to secure the metal contact lens holder. Viscoat® (125 $\mu$L) was then applied to the cornea followed by the placement of a wide angle lens onto the cornea. The vitreous was then removed using the SERIES TEN THOUSAND® OCUTOME® posterior-segment surgical system for 10 minutes by a combination of cutting (500 cuts/minute) and suction (90 mm Hg), while continually supplying BSS® or BSS Plus® irrigating solution, or an irrigating solution containing Compound X (1.0 $\mu$M) (at room temperature), at a rate of approximately 3.5 mL/minute and an ocular fluid pressure of 35 mm Hg. Upon completion of the surgery, instruments were withdrawn, infusion pressure reduced to 22 mm Hg, sclerotomies closed, and the conjunctiva reapproximated at the limbus with sutures. A typical surgical procedure required approximately 40–50 minutes, utilizing approximately 100 mL of irrigation solution. The amount of vitreous replaced was approximately 1.5 mL. At various times following vitrectomy, lenses were excised and immediately examined by low resolution light microscopy. Photographs were taken with a digital camera for a later assessment of line suture defects.

The results of this study document the early development of PSC in the Dutch Belted rabbit following vitrectomy, as quantified by scoring for the presence of distorted suture branches and sub-branches. Kinetic studies demonstrated that shortly following vitrectomy the rate of lens growth was slightly depressed in all animals that underwent surgery when compared to the naive controls. The rate of lens growth in animals treated with the Compound X-supplemented therapeutic irrigation solution during vitrectomy was essentially identical to that of naive controls from 3–12 months post-surgery. Comparison of the effect of vitrectomy with standard irrigation and the Compound X-supplemented irrigation 3 month post-surgery indicated a high incidence of an acute distortion of normally straight line sutures for animals of the standard irrigation treatment groups (Table 1) but not the Compound X treated animals. By six months post-surgery, lenses from the standard irrigation treatment groups exhibited multiple small sub-branches extending from the main crooked lens suture branches. This abnormal condition was further aggravated at twelve months post-vitrectomy, as recognized by the extension of existing sub-branches and the development of additional small sub-branches. In marked contrast, however, lenses from animals irrigated with Compound X therapeutic irrigation solution exhibited only slightly distorted suture branches which, on average, were devoid of sub-branches. This condition was essentially maintained throughout twelve months post-vitrectomy.

Using a scoring scale that captures the "crookedness" of the posterior lens line suture and number of suture sub-branches, it was evident at 12 months that the incidence of lens-suture defect development following standard irrigation was greater than that following irrigation with Compound X. Of the standard irrigation-treated lenses, 93% (or 14 out of 15 lenses) exhibited lens suture defect development, with an average suture defect score of +3.5 (minimum score, 0=a straight line suture; maximum score, +6=to a very crooked suture pattern with ten (or more) small sub-branches or eight (or more) large sub-branches or a mature cataract). In contrast, 86% (or 6 out of 7 lenses) of the lenses from the Compound X treatment group were unaffected by vitrectomy with an average suture defect score of +1.7 at this same time point. The lens scores of animals treated with the Compound X supplemented therapeutic irrigation solution were essentially identical to those of naive controls (score$_{avg}$=+1.63). The Compound X supplemented therapeutic irrigation solution is the first known agent to effectively suppress vitrectomy-induced PSC formation.

TABLE 1

Incidence of Posterior Subcapsular Cataract Formation in Rabbit Following Vitrectomy

| Time of Analysis | Vitrectomy (irrigating solution only) | Vitrectomy (irrigating solution w/1.0 $\mu$M Compound X) |
|---|---|---|
| | Incidence of Lens Line Suture Distortion | |
| 3 month post-Vitrectomy | 12/16 | 0/8 |
| 6 month post-Vitrectomy | 13/16 | 1/7 |
| 12 month post-Vitrectomy | 14/15 | 1/7 |

What is claimed is:

1. A method for the treatment, prevention or amelioration of post-surgical formation of posterior subcapsular cataract or posterior capsule opacification which comprises administering to a mammal prior to, during or following surgery, or combinations thereof, one or more composition(s) comprising a pharmaceutically acceptable vehicle and a therapeutically effective amount of a compound of formula (I):

$$A—X—(CH_2)_n—Y—(CH_2)_m—Z \quad (I)$$

wherein:
- A is an non-steroidal anti-inflammatory agent (NSAIA) originally having a carboxylic acid;
- A—X is an ester or amide linkage derived from the carboxylic acid moiety of the NSAIA, wherein X is O or NR;
- R is H, $C_1$–$C_6$ alkyl or $C_3$–$C_6$ cycloalkyl;
- Y, if present, is O, NR, $C(R)_2$, CH(OH) or $S(O)_{n'}$;
- n is 2 to 4 and m is 1 to 4 when Y is O, NR, or $S(O)_{n'}$;
- n is 0 to 4 and m is 0 to 4 when Y is $C(R)_2$ or is not present;
- n is 1 to 4 and m is 0 to 4 when Y is CH(OH);
- n' is 0 to 2; and
- Z is:

wherein:
A is

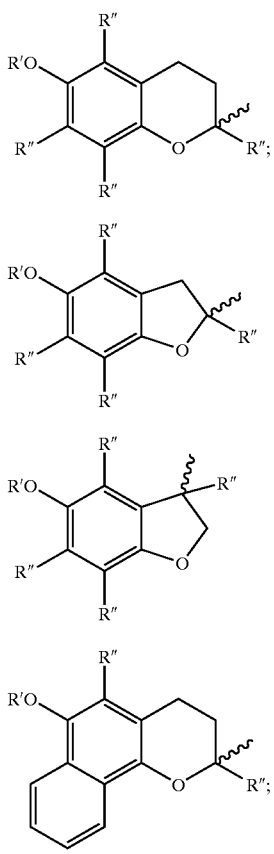

a b c d wherein:
- R' is H, C(O)R, $C(O)N(R)_2$, $PO_3^-$, or $SO_3^-$; and
- R" is H or $C_1$–$C_6$ alkyl; and pharmaceutically acceptable salts therefor.

2. A method according to claim 1, wherein the compound of formula (I) is selected from the group consisting of compounds wherein:
- X is O or NR;
- R is H or $C_1$ alkyl;
- Y is CH(OH), and m is 0 to 2 and n is 1 or 2, or Y is not present, and m is 1 or 2 and n is 0 to 4;
- Z is a, b or d;
- R' is H or $C(O)CH_3$; and
- R" is $CH_3$.

3. A method according to claim 1, wherein the compound of formula (I) is selected from the group consisting of compounds wherein the non-steroidal anti-inflammatory agent is selected from the group consisting of: fenamic acids; indoles; and phenylalkanoic acids.

4. A method according to claim 1, wherein the compound of formula (I) is selected from the group consisting of compounds wherein the non-steroidal anti-inflammatory agent is selected from the group consisting of: loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

5. A method according to claim 4, wherein the compound of formula (I) is selected from the group consisting of compounds wherein:
- X is O or NR;
- R is H or $C_1$ alkyl;
- Y is CH(OH), and m is 0 to 2 and n is 1 or 2, or Y is not present, and m is 1 or 2 and n is 0 to 4;
- Z is a, b or d;
- R' is H or $C(O)CH_3$; and
- R" is $CH_3$.

6. A method according to claim 4, wherein the compound of formula (I) is selected from the group consisting of compounds wherein the non-steroidal anti-inflammatory agent is selected from the group consisting of naproxen, flurbiprofen and diclofenac.

7. A method according to claim 1, wherein the compound of formula (I) is selected from the group consisting of:

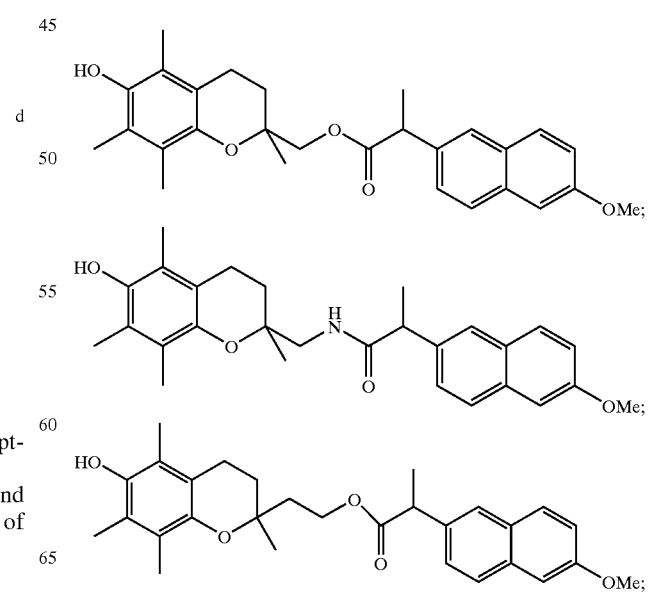

-continued

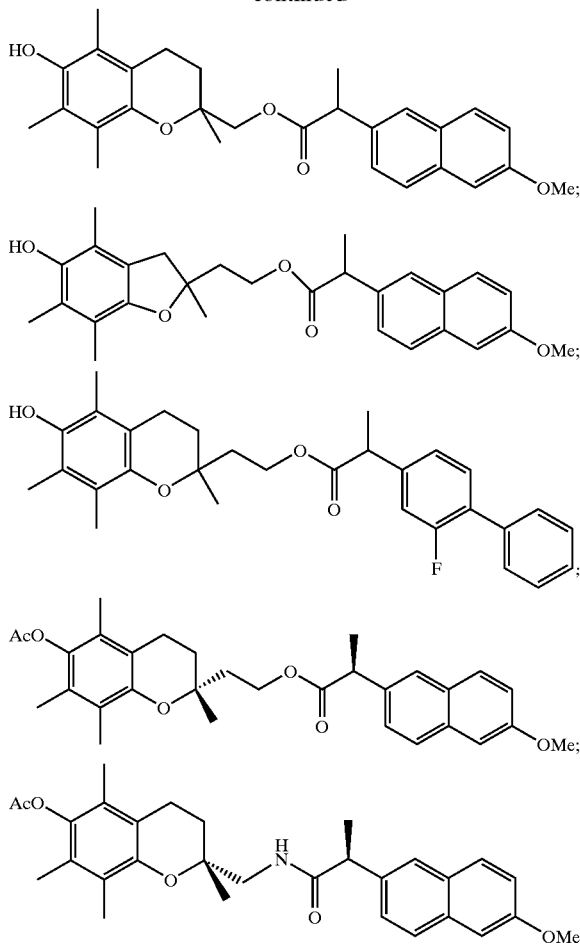

and sterioisomers thereof.

8. A method according to claim 1, wherein the compound of formula (I) is:

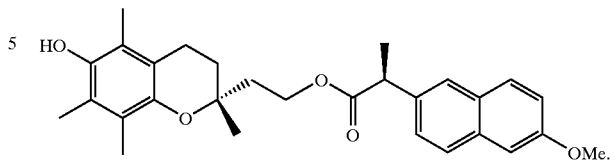

9. A method according to claim 6, wherein the compound of formula (I) is selected from the group consisting of compounds wherein:
X is O or NR;
R is H or $C_1$ alkyl;
Y is CH(OH), and m is 0 to 2 and n is 1 or 2, or Y is not present, and m is 1 or 2 and n is 0 to 4;
Z is a, b or d;
R' is H or $C(O)CH_3$; and
R" is $CH_3$.

10. A method according to claim 1, wherein the composition(s) is/are a topical ophthalmic or physiologically balanced irrigating solution, or a combinations thereof.

11. A method according to claim 4, wherein the composition(s) is/are a topical ophthalmic or physiologically balanced irrigating solution, or a combinations thereof.

12. A method according to claim 8, wherein the composition(s) is/are a topical ophthalmic or physiologically balanced irrigating solution, or a combinations thereof.

13. A method according to claim 1, wherein the surgery is vitrectomy, cataract or refractive surgery.

14. A method according to claim 4, wherein the surgery is vitrectomy, cataract or refractive surgery.

15. A method according to claim 8, wherein the surgery is vitrectomy, cataract or refractive surgery.

16. A method according to claim 13, wherein the surgery is vitrectomy.

* * * * *